United States Patent [19]

Blanke

[11] 4,031,747
[45] June 28, 1977

[54] MISFIRE MONITOR FOR ENGINE ANALYSIS HAVING AUTOMATIC RESCALING

[75] Inventor: John David Blanke, Fullerton, Calif.

[73] Assignee: Beckman Instruments, Inc., Fullerton, Calif.

[22] Filed: Aug. 16, 1976

[21] Appl. No.: 714,143

[52] U.S. Cl. .................................. 73/116; 73/23
[51] Int. Cl.² ......................................... G01M 15/00
[58] Field of Search ............ 73/116, 23, 117.3, 117; 23/288 F, 232 E; 60/277

[56] References Cited
UNITED STATES PATENTS

| | | | |
|---|---|---|---|
| 3,938,479 | 2/1976 | Oberstadt | 73/116 X |
| 3,969,932 | 7/1976 | Rieger et al. | 73/118 |

Primary Examiner—Jerry W. Myracle
Attorney, Agent, or Firm—R. J. Steinmeyer; P. R. Harder; D. A. Streck

[57] ABSTRACT

An improvement to a misfire monitor sensing lean-roll in an internal combustion engine by comparing the rate of change in $O_2$ in the exhaust gases with respect to time against a limit is disclosed. In the preferred embodiment, the sensed $O_2$ level in the exhaust is used as an input to rescaling means which automatically normalizes the values used in the comparison to a standard range. Normalization is accomplished alternately by rescaling the rate of change value, rescaling the limit value used, or diluting the exhaust gases sampled to the level of a "standard" air blown engine to which the comparison limit is scaled.

7 Claims, 8 Drawing Figures

MISFIRE MONITOR FOR ENGINE ANALYSIS HAVING AUTOMATIC RESCALING

BACKGROUND OF THE INVENTION

Control of emissions from motor vehicles is now an accepted and necessary automotive design consideration throughout the world. In the United States since about 1965 (and earlier in California) all motor vehicles sold have incorporated some form of emission control. Recently, more vehicles sold for use in countries other than the United States have also been designed to reduce pollutants. The speed with which engine design changes have taken place to satisfy pollution reduction requirements has been extraordinary. Not only have the engine and vehicle manufacturers had to engage in major expenditures for facilities, equipment and accelerated technical achievement, but similarly, the automotive service industry has been experiencing a major upheaval in the effort to provide continuing qualified engine malfunction diagnosis and maintenance capability.

Exhaust emission standards in the United States have become increasingly stringent. Concurrent with the emphasis on reducing emissions, the automotive service industry throughout the world was beginning to acquire exhaust analyzers for measurement of hydrocarbons (HC) and/or carbon monoxide (CO). Now, the majority of qualified automobile service centers, particularly in the United States, use HC/CO analyzers routinely as an important diagnostic aid and also to inspect or verify vehicle manufacturer specifications at idle. In a number of areas withing the United States, legislation requires service garages to have an approved HC/CO analyzer. CO analyzers have also become a mandatory part of emission controls programs in a number of countries other than the United States.

Service facilities have found emission analyzers a useful diagnostic/service device during routine service inspection. For example, the use of a CO analyzer for properly adjusting carburetor balance and air/fuel ratios is now standard practice. Hydrocarbon measurements as an indication of ignition problems, a malfunctioning exhaust or intake valve, etc., is also widely used as a quick method of screening vehicles for further diagnosis by conventional oscilloscope testers.

The stringent standards in the United States for 1975 have forced most automobile manufacturers to use catalytic converters on current production vehicles to provide adequate control of exhaust emissions of hydrocarbons and carbon monoxide. Unfortunately, the effective use of HC/CO exhaust gas analyzers as a diagnostic aid for vehicles equipped with catalytic converters is more complicated than for vehicles without converters. In fact, if the converter is working properly, engine diagnosis with HC/CO analyzers is extremely difficult unless the vehicle has an exhaust sampling port ahead of the converter. When the catalytic converter is functioning properly, it oxidizes essentially all of the HC and CO to $CO_2$ and water vapor. Consequently, the concentrations in the exhaust are so low they cannot be measured with accuracy with existing "garage-type" instruments. The changes in raw exhaust concentrations of HC, for example, as a result of intermittent misfire or "lean-roll", no longer appear in the converted exhaust gases and the conventional exhaust gas analyzer loses value as a diagnostic tool.

The detection of a lean-roll condition is becoming of great concern not only to the service garage owner doing fter sale service, but, to the automobile manufacturer and his dealers as well. The leaner the mixtue at which the carburetor is set, the greater the economy when the engine is operating in the manner for which it was designed. A slight deviation, however, can put the engine in a lean-roll condition which increases both gasoline consumption and the emission of pollutants at the exhaust. The phenomenon of lean-roll can best be understood with reference to FIG. 1. In a typical engine 10 having cylinders 12, a common intake manifold 14 is connected from a carburetor 16 to the intake ports 18 of cylinders 12. Obviously, the distance from the two outside cylinders 12 is greater than the distance to the two inside cylinders 12. The variations in the distances that the gasoline/air mixture must travel through the manifold 14 to reach the various cylinders 12 causes a difference in the mixture at the various cylinders 12 even though produced by a common carburetor 16. The mixture at the inner cylinders 12 tends to be richer than the mixture at the outer cylinders 12. In order to ignite and burn properly in the cylinders 12 the gasoline to air ratio of the fuel mixture must be within certain high and low limits. As the mixture is made more lean (less gasoline to a fixed volume of air) a point will be reached where the mixture will not ignite.

Since, as stated earlier, the mixture at the two outer cylinders 12 tends to be leaner, as the mixture at the carburetor 16 is adjusted leaner, the two outer cylinders 12 will reach a point where they cyclically begin to misfire. This is called the "lean-roll" condition. As the mixture received drops below the critical level, the outer cylinders 12 misfire. This condition can occur individually or simultaneously as the exact mixture in any cylinder 12 at any instant is a function of many factors including the mixture at the carburetor at that instant (which may vary), the temperature of the manifold 14, whether the cylinder 12 fired on the last power cycle, and the amount of dilutants retained from the exhaust cycle during the intake stroke. Lean mixture can, of course, occur at all the cylinders 12 but we are concerned here with the slow roll phenomenon which is more correlatable to the outside cylinders (those furthest from the carburetor) in any engine.

In an application for United States Letters Patent titled IMPROVED ENGINE ANALYSIS APPARATUS filed concurrently herewith in the names of John D. Blanke et al. and assigned to the common assignee of this application, a misfire monitor is described which is capable of detecting lean-roll in an internal combustion engine by comparing the rate of change of $O_2$ in the exhaust gases with respect to time ($dO/dt$) against a limit. Various factors associated with different engines, such as air blowing, make the valve of $dO/dt$ during an actual lean-roll condition a variable item. In order to prevent false indications, it is preferable to have the $dO/dt$-limit value comparison made particularly adapted to the engine under analysis. In production line situations of engine analysis, roadside checks by enforcement agencies involving numerous automobile types, or similar situations, it is desirable that any instrumentation minimize the requirements for operator intervention or decision making. Further, air leaks into the exhaust system can make the actual $O_2$ content of an engine's exhaust be outside the range expected. In such instances, self-regulating equipment can be used to good advantage.

Therefore, it is the object of the present invention to provide a misfire monitor capable of automatically adjusting the parameters used in the testing for a lean-roll condition to a standard range whereby the misfire monitor can be used on various engine types with little or no operator intervention.

SUMMARY OF THE INVENTION

In engine exhaust gas analysis apparatus having a sensor for determining the content of oxygen or the like in the exhaust, differentiating means to monitor the rate of change of oxygen with respect to time ($dO/dt$), a comparator for comparing $dO/dt$ to a limit, and an alarm to indicate to an operator when $dO/dt$ exceeds the limit (indicating a lean-roll condition in the engine) the present invention provides readjustment to compensate for various engine types. Means are provided to cause the values used in the comparator to be normalized to the range of a "standard" engine. In the preferred embodiment, $O_2\%$ in the exhaust gas is used as an input to rescaling means. The rescaling means automatically rescales either the limit value or $dO/dt$ as a function of $O_2\%$. In an alternate embodiment, air is automatically mixed with the exhaust gases prior to the sensor to normalize the exhaust gases at the sensor to appear as if from the standard engine. Alternate approaches to rescale or normalize on a manual and semi-automatic basis are disclosed.

DESCRIPTION OF THE PREFERRED EMBODIMENT

Figure 2:
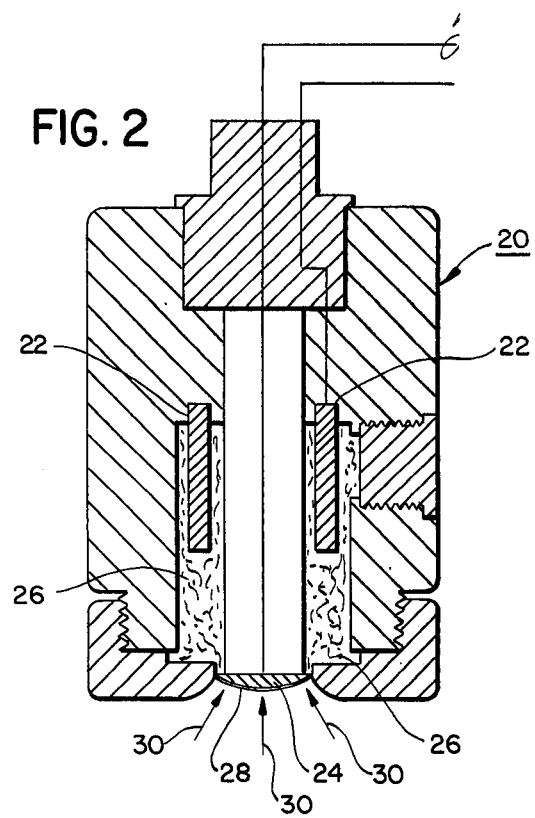
FIG. 2 is a cross-sectional elevation of a sensor for oxygen for use with the present invention.

It was found that an oxygen analyzer can be combined with the HC/CO analyzer to restore the value of exhaust gas analysis for engine diagnostic purposes since the quantity of $O_2$ is not affected by the catalytic converter. Thus, $O_2$ analysis is available whether or not the vehicle is equipped with a catalytic converter and whether or not the vehicle uses a secondary air pump. This is discussed in greater detail in the copending application IMPROVED ENGINE ANALYSIS APPARATUS mentioned above. To accomplish the objectives of that disclosed invention, it is necessary to employ a fast response oxygen analyzer (90% in five seconds or better). It is possible by techniques known in the art to provide a sensor and associated electronics capable of such fast response oxygen sensing. Such equipment is manufactured by the assignee of the present application. Basically, such analysis apparatus is simple. Of course, certain proprietary techniques allow one oxygen analyzer to operate more efficiently than another. Referring to FIG. 2, in a sensor 20 two electrodes 22 and 24 are separately mounted within a body and are electrically connected by an electrolyte 26. A constant potential is impressed across the two electrodes 22 and 24. A gas-permeable membrane 28 separates the electrodes 22 and 24 from the exhaust sample 30 and fits firmly against the cathode electrode 24. Oxygen from the sample 30 diffuses through the membrane 28 and is reduced at the cathode 24. The resultant electrical current flow between the anode electrode 22 and cathode 24 is proportional to the partial pressure of oxygen in the sample 30. The sensor 20 is placed in the exhaust stream to sense the partial pressure of oxygen. A potential of 0.725 volts DC is applied across the cathode 24 and anode 22 to make the sensor oxygen selective by techniques well known in the art. When the oxygen in the exhaust stream 30 diffuses through the membrane 28, it is reduced at the cathode 24. The reduction of oxygen results in a current flow proportional to the partial pressure of oxygen in the sample. When no oxygen is present, no electrical current flows in the sensor 20. When oxygen is present, electrical current flows in the sensor 20 according to the polarographic oxygen curve for the potential across the electrodes 22 and 24. The magnitude of this current is dependent upon the partial pressure of oxygen in the sample being analyzed.

Figure 3:
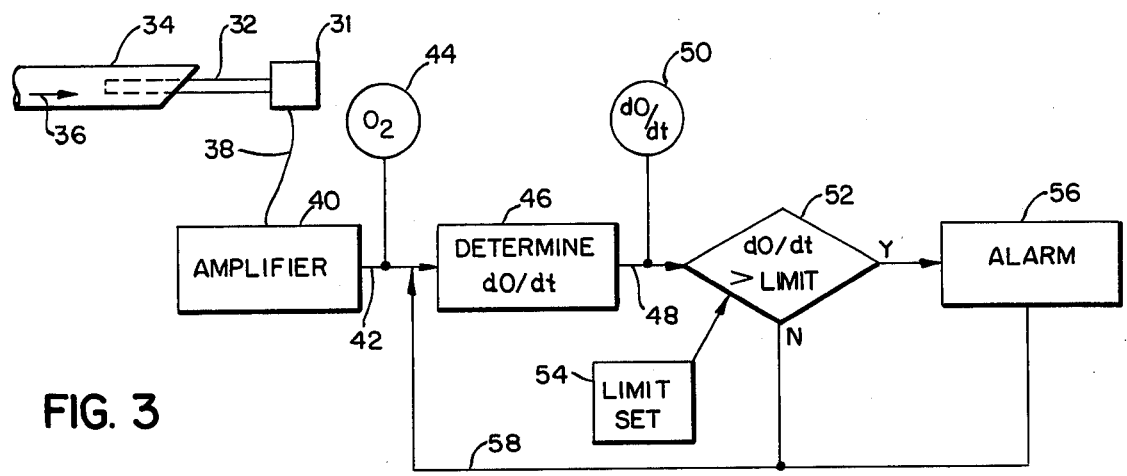
FIG. 3 is a block diagram of the apparatus comprising the present invention.

Referring now to FIG. 3, a misfire monitor as wherein the present invention is employed is shown as having a sensor 31 connected to a probe 32 adapted to be inserted in the exhaust pipe 34 of an automobile (not shown) and thereby conduct a portion of the exhaust gases 36 to oxygen sensor 31. Sensor 31 is connected by appropriate connection means 38 to amplifier means 40. The only limitation on sensor 31 and amplifier 40 is that they behave as a fast response oxygen analyzer. That is, a change in the quantity of oxygen in exhaust gas 36 should be responded to and indicated at least to the 90% level in at least five seconds. The essential quality thus achieved is the ability to respond to changes in $O_2$ level as a result of lean-roll while rejecting short term transient spikes by this "chemical capacitor" behavior. If sensor 31 and amplifier 40 are incapable of fast response to changes in oxygen, either through damping factors or inherent design limitations, the misfire monitor will present meaningless or erroneous data to the user. The output 42 of amplifier 40, indicating the instantaneous quantity of oxygen in exhaust gas 36 as sensed by sensor 31, is connected to drive an indicating meter 44 which continuously displays the quantity of oxygen in percent in the exhaust gas 36. The output 42 of amplifier 40 is also made an input to appropriate means 46 for determining the rate of change ($dO/dt$) of oxygen in the exhaust gases 36. $dO/dt$ determination means 46 can be either analog or digital circuitry well known to persons skilled in the art. The output 48 of the $dO/dt$ determination means 46 is connected to $dO/dt$ indicating meter 50 for indicating the instantaneous rate of change of the oxygen content of exhaust gases 36 to the operator. Additionally, the instantaneous value of $dO/dt$ appearing at output 48 is also connected to limit comparison means 52. As with $dO/dt$ determination means 46, limit comparison means 52 can be provided by either analog or digital circuitry well known to those skilled in the art. Limit set means 54 is provided and connected to limit comparison means 52 so that the operator can select the limit at which the comparison will be made. Such factors as air pumping or non-air pumping and the number of cylinders in the engine may be used in determining the limit value as will be hereinafter discussed in greater detail. When the instantaneous value of $dO/dt$ is greater than the limit presently being used by limit comparison means 52, alarm 56 connected to limit comparison means 52 is activated to provide an audible and/or visible indication to the operator. The determination of $dO/dt$ by means 46 and the comparison against the limit by limit comparison means 52 is a constant repetitive loop function as represented by the closed loop logic line 58 from limit comparison means 52 and alarm 56.

Figure 4:
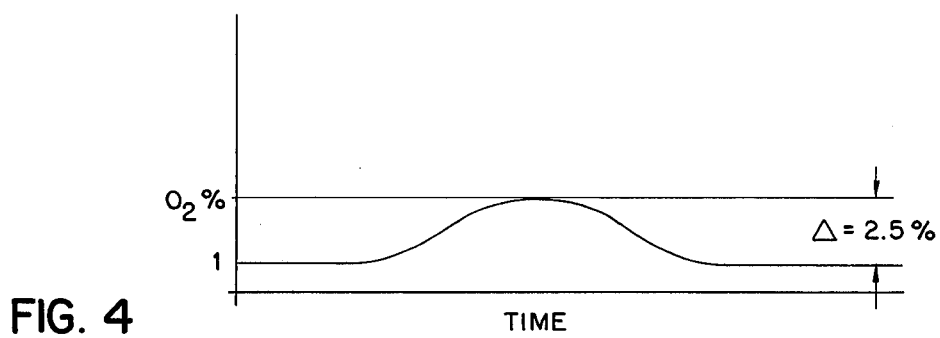
FIG. 4 is an illustration of the change in oxygen level in the exhaust of a non-airpumped engine during a lean-roll condition.
Figure 5:
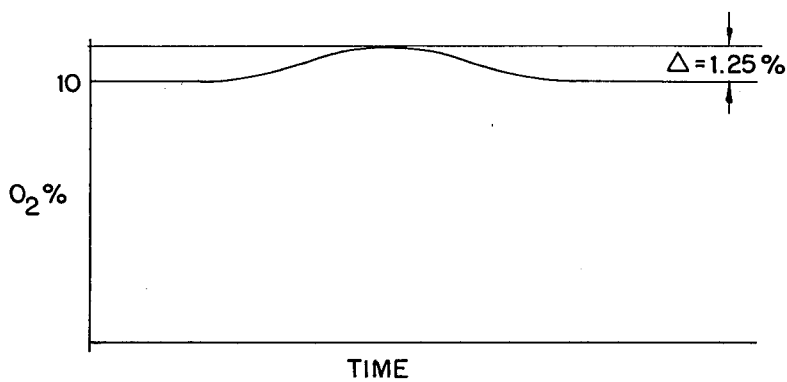
FIG. 5 is an illustration of the change in oxygen level in the exhaust of an airpumped engine during a lean-roll condition.

Referring now to FIG. 4 and FIG. 5, a further consideration in the detection of the lean-roll condition is illustrated. In FIG. 4, a single lean roll increase in $O_2\%$ is shown for an engine without additional air pumping provisions. Normal atmosphere contains approximately 21% $O_2$. In an engine without additional air pumping provisions, the $O_2$ content of the exhaust gas with all cylinders firing normally is approximately 1%. During a lean-roll condition a spike increase in the $O_2$ level will occur in the exhaust gases over a total period of rise and fall of perhaps 10 seconds. The magnitude of the change in $O_2$ level will be according to the contribution of the non-firing cylinder to the firing cylinders in the total exhaust gas stream. In other words, the 1% $O_2$ content exhaust gases from the firing cylinders will dilute the 21% $O_2$ content exhaust gas from the non-firing cylinder on a proportional basis. Thus, in an eight cylinder engine, a lean-roll condition in a single cylinder will cause an increase in the $O_2$ level of the exhaust gases of about 2.5%. When $dO/dt$ is sensed, this will be seen as a substantial rate change.

By comparison, FIG. 5 shows the change resulting from a lean-roll condition in an engine equipped with additional air pumping capability. If the same eight cylinder engine discussed above were equipped with additional air pumping means, the exhaust, when the engine was running normally, would contain approximately 7-10% $O_2$ instead of the 1% without air pumping. If, for ease of calculation, we assume the 10% $O_2$ normal state, then taking into consideration the dilution effect of the pumped air with 21% $O_2$ and the raw exhaust gases leaving the piston chamber which were indicated to be 1%, the exhaust must be approximately one-half raw exhaust gases and one-half pure air. This being the case, when the lean-roll condition does occur as before, the raw exhaust gases will increase in $O_2$ content by the same 2.5%. Because of the dilution by the pumped air, however, the change in $O_2$ at the exhaust pipe will be only 1.25% with an attendant $dO/dt$ only one-half that in the non-air pumped engine during lean-roll.

It is these dilution effects of air-pumping or the like and the change in $dO/dt$ which can be expected as a result of a lean-roll condition which determine the limit value to be used in the $dO/dt$-limit comparison. The greater the number of cylinders in the engine, the smaller the change in $O_2\%$ as a result of a lean-roll condition. Thus, the $dO/dt$ value will also be less. To make the simplest system (such as that of FIG. 3 but without limit set means 54), the limit value is chosen for the smallest $dO/dt$ value which will be encountered indicating a true lean-roll condition. If the change in an eight cylinder air-blown engine is used as the standard, any non-air blown engine or engine of fewer cylinders will have a $dO/dt$ greater than the limit chosen to validly indicate lean-roll in the standard engine. In such a simplified, general purpose instrument, however, sensitivity becomes a potential problem. Having set the limit at the lowest value, changes in $dO/dt$ in non-air blown engines and engines of fewer cylinders not representing an actual lean-roll condition may, nevertheless, exceed this minimal value and signal a lean-roll condition. The limit set means 54 of FIG. 3 is provided to eliminate this problem by allowing the limit to be varied by the operator as by switches or the like as a function of such parameters as number of cylinders, air-blown/non-air blown, etc.

Figure 6:
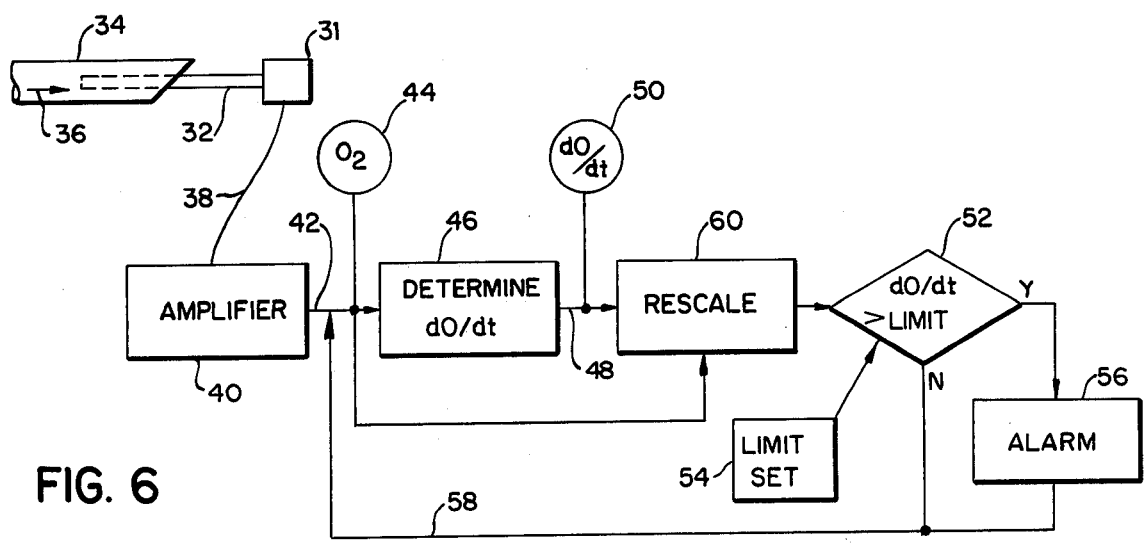
FIG. 6 is a block diagram of an alternate embodiment of the present invention including $dO/dt$ rescaling to automatically compensate for various engine types.
Figure 7:
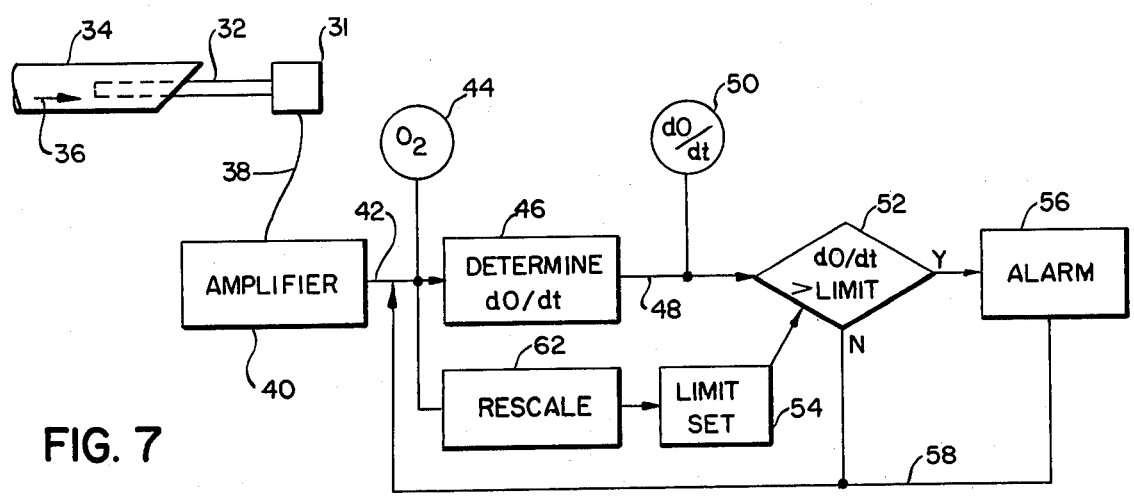
FIG. 7 is a block diagram of an alternate embodiment of the present invention including limit rescaling to automatically compensate for various engine types.

The typical engine test environment, particularly on a production line, is such that it is desirable for any apparatus used to require as little operator intervention as possible. The variations in base level $O_2\%$ (when $dO/dt = 0$) in the exhaust gases of various engines as described above can be used to good effect in this regard. Thus, in the preferred embodiment of the present invention, automatic adjustment is made for different engines as a function of the "normal" $O_2$ level in the exhaust. As previously described, the lean-roll condition is sensed by comparing the rate of change in $O_2$ level against a limit. If $dO/dt$ in a lean-roll condition is different in various engines and normalizing to a standard is required, several methods can be employed. First, the rate of change can be rescaled to a standard range as a function of engine type. Alternatively, the limit against which the rate of change is compared can be rescaled to correspond to the range of $dO/dt$ swing in the lean-roll condition, again as a function of engine type. These alternate approaches as applied to the present invention are shown in FIG. 6 and FIG. 7. In the embodiment of FIG. 6, the value of $dO/dt$ being used in limit comparison means 52 is rescaled by rescaling means 60 as a function of the $O_2\%$ level appearing at output 42 of amplifier 40. In the embodiment of FIG. 7, the $O_2\%$ level appearing at the output 42 of amplifier 40 is applied to rescaling means 62 which is operably connected to limit set means 54. Rescaling means 62 causes limit set means 54 to reset the limit value being used to a rescaled value as a function of the value of the $O_2\%$ level being input to rescaling means 62.

By way of example, if the total lean-roll rise and fall in $O_2\%$ of FIGS. 4 and 5 lasts for 10 seconds and if a straight ramp is assumed for ease of calculation, then the $O_2\%$ level of FIG. 4 rises 2.5% in 5 seconds giving a $dO/dt$ of 2.5/5 or 0.5. Correspondingly, under the same assumptions, the $O_2\%$ level of FIG. 5 rises 1.25% in 5 seconds giving a $dO/dt$ of 1.25/5 or 0.25. An appropriate limit value to use in conjunction with an engine behaving like that represented by FIG. 4 might be 0.4. That is, when $dO/dt$ exceeds 0.4 a lean-roll is in progress. Thus, when the base level of $O_2$ is 1%, an unscaled $dO/dt$ should be compared to an unscaled limit of 0.4. If the apparatus were used in the same configuration on an engine behaving in the manner of FIG. 5, however, rescaling would be required to detect the lean-roll condition. Since the change in $dO/dt$ is one-half that of the engine of FIG. 4 (assuming the engine of FIG. 4 to be the "standard"), one-half is the appropriate scaling factor to apply. Thus, in the approach to rescaling of FIG. 6, when a base $O_2$ level of 10% is detected, the value of $dO/dt$ should be doubled before limit checking since it is only one-half the value needed for valid comparison to the limit value of 0.4. On the other hand, to use the approach of FIG. 7, when a base $O_2$ level of 10% is detected, the alarm limit value of 0.4 should be divided in half since it is twice as big as it should be for a valid comparison to the $dO/dt$ value being compared. The same approach would be taken with any additional engine types that might arise having different base $O_2$ levels and different rises in $dO/dt$ during the lean-roll condition.

While in the preferred embodiments shown in FIGS. 6 and 7 the rescaling accomplished by rescaling means 60 or 62 is accomplished automatically in response to an input from amplifier 40 indicating the $O_2$% base level, the desired results can be accomplished manually or semi-automatically. The only requirement is that the $dO/dt$-limit comparison made in limit comparison means 52 be normalized to a standard engine. That is, a standard test for lean-roll is to be accomplished by limit comparison means 52 regardless of engine type with the inputs to the test being rescaled or normalized to the range of the "standard". Thus, rescaling means 60 and 62 could include adjusting means for directly setting the value of $dO/dt$ and/or the limit value to the normalized values or, alternatively, for setting the engine type whereupon the normalized values would be provided in a semi-automatic manner by the balance of the circuitry comprising rescaling means 60 and 62.

Figure 8:
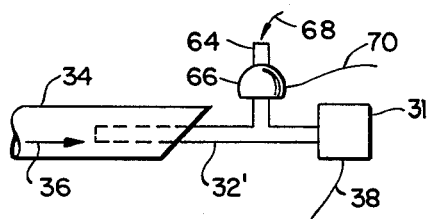
FIG. 8 is a simplified drawing of a modified probe for sampling exhaust gases wherein an air bleed is provided to allow automatic normalizing of the input to the sensor to a standard range.
Figure 1:
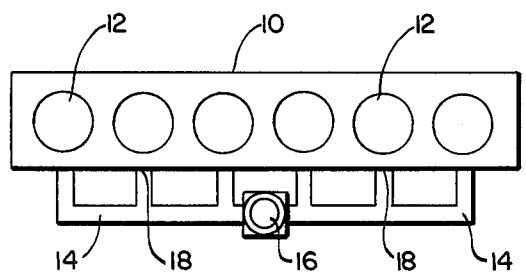
FIG. 1 is a simplified top view of an engine showing the difference in distances traveled by the fuel-air mixture between the carburetor and the various cylinders.

Normalization to a standard could also be accomplished by the modified probe 32' shown in FIG. 8. In probe 32' an air bleed inlet 64 having adjustable valve means 66 incorporated therein is fit into probe 32' in a manner as shown so as to allow air 68 to be mixed with exhaust gases 36 prior to sensor 31. If the test made in limit comparison means 52 is standardized to an air-blown engine, the input to the test can be normalized to the standard by adjusting valve means 66 to mix air 68 with exhaust gases 36 in an amount sufficient to achieve a base level $O_2$% equal to that in the "standard" air-blown engine. This could be done manually, but, preferably, is done automatically by connecting feedback means 70 to the output 42 of amplifier 40 whereby valve means 66 is automatically actuated to a standard setpoint value of $O_2$% as a function of the feedback signal representing $O_2$%.

Having thus described my invention, I claim:

1. In engine exhaust gas analysis apparatus having:
    means for sampling the exhaust gases including means for generating a first signal indicating the amount of a component present in the exhaust gases;
    differentiating means connected to said sampling means and including means responsive to said first signal for generating a second signal indicating the rate of change of said first signal with respect to time;
    means connected to said differentiating means for comparing said second signal to a limit; and,
    means connected to said comparing means for indicating when said second signal exceeds said limit, the improvement comprising:
    means for causing the values of said second signal and said limit to be normalized to a standard range before said comparing is done whereby the exceeding of said limit by said second signal will have substantially the same meaning regardless of the engine being analyzed.

2. Improved engine exhaust gas analysis apparatus as claimed in claim 1 wherein:
    said component in the exhaust gases in oxygen.

3. Improved engine exhaust gas analysis apparatus as claimed in claim 1 wherein said normalizing means comprises:
    said differentiating means including means for rescaling said second signal as a function of said first signal.

4. Improved engine exhaust gas analysis apparatus as claimed in claim 1 and comprising additionally:
    means for setting said limit connected to said comparing means; and,
    means for rescaling said limit as a function of said first signal connected between said sampling means and said limit setting means.

5. The improved method of detecting a lean-roll condition in an internal combustion engine comprising the steps of:
    a. sampling the exhaust gases from the engine to produce a first signal indicative of the percent of oxygen contained therein;
    b. differentiating said first signal to produce a second signal indicative of the time rate of change of said first signal;
    c. normalizing the second signal value and a limit value to a standardized range representing a lean-roll condition;
    d. comparing said second signal to said limit value such that if said second signal exceeds said limit value the engine is in a lean-roll condition; and,
    e. activating means for indicating a lean-roll condition when said second signal exceeds said limit value.

6. The method of claim 5 wherein said step of normalizing comprises the steps of:
    a. determining the base level of said first signal when said second signal equals zero; and,
    b. rescaling the value of said second signal as a function of said base level whereby a single limit value can be used in detecting lean-roll in engines having differing levels of time rate of change of said first signal during a lean-roll condition.

7. The method of claim 5 wherein said step of normalizing comprises the steps of:
    a. determining the base level of said first signal when said second signal equals zero; and,
    b. rescaling the value of said limit value as a function of said base level whereby a single amplification level can be used in producing said second signal when detecting lean-roll in engines having differing levels of time rate of change of said first signal during a lean-roll condition.

* * * * *

UNITED STATES PATENT OFFICE
CERTIFICATE OF CORRECTION

Patent No. 4,031,747  Dated June 28, 1977

Inventor(s) John David Blanke

It is certified that error appears in the above-identified patent and that said Letters Patent are hereby corrected as shown below:

Column 8, line 12, "in", second occurrence, should read -- is --.

Signed and Sealed this

Fourth Day of April 1978

[SEAL]

Attest:

RUTH C. MASON
Attesting Officer

LUTRELLE F. PARKER
Acting Commissioner of Patents and Trademarks